United States Patent [19]
Rauckman et al.

[11] Patent Number: 5,958,836
[45] Date of Patent: Sep. 28, 1999

[54] ALGISTATS

[75] Inventors: Elmer Rauckman, Fleminton, N.J.; Michael T. Sheehan, Corpus Christi; William W. Wilkison, Richardson, both of Tex.

[73] Assignee: TriQuest, LP, Dallas, Tex.

[21] Appl. No.: 09/161,264

[22] Filed: Sep. 26, 1998

[51] Int. Cl.$^6$ .................................................... A01N 33/10
[52] U.S. Cl. ......................... 504/160; 514/653; 564/360
[58] Field of Search ........................... 504/160; 514/653; 564/360

[56] References Cited

U.S. PATENT DOCUMENTS

| | | | |
|---|---|---|---|
| 3,808,257 | 4/1974 | Richter | 260/465 E |
| 3,842,179 | 10/1974 | Bordenca | 424/330 |

*Primary Examiner*—Brian M. Burn
*Attorney, Agent, or Firm*—Donald R. Cassady

[57] ABSTRACT

The present invention relates to a method for the prevention of growth of algae by incorporating within liquids or coating on surfaces certain substituted amino alcohols. More precisely, this invention provides for algistat end uses for amino alcohol compounds endowed with chain extension which have the general formula:

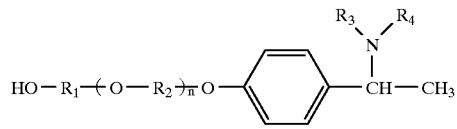

wherein n is 1–1000; and $R_1=R_2$, and $R_1$ and $R_2$ are from the group consisting of —$CH_2$—$CH_2$—; —$CH_2$—$C(CH_3)H$—; and —$C(CH_3)H$—$CH_2$—; $R_3$, and $R_4$ are each independently selected from the group consisting of H, —$CH_3$, —$CH_2CH_3$, —$CH_2OH$, and —$CH_2$—$CH_2$—$OH$; and the diasteromeric salts thereof.

5 Claims, No Drawings

ALGISTATS

BACKGROUND OF THE INVENTION

1. Field of the Invention

The present invention relates to a new use of a class of amino alcohols as algistats.

2. Description of Related Art

The following prior art references are disclosed in accordance with the terms of 37 CFR 1.56, 1.97, and 1.98.

U.S. Pat. No. 5,169,848, issued Dec. 8, 1992, to Bettarini et al., discloses new pyridazinones endowed with insecticidal and acaricidal activity.

U.S. Pat. No. 3,520,931, issued Jul. 21, 1970, to d'Ostrowick et al., discloses a process for resolving a mixture of optical antipodes of a primary alpha-aralkylamine in which one of these antipodes predominates.

U.S. Pat. No. 5,011,996, issued Apr. 30, 1991, to Kiel et al., discloses reaction products of oxo compounds and amines or ammonia, such as (-(p-Chlorophenyl)-ethylamine (Example 1 therein).

U.S. Pat. No. 4,394,496, issued Jul. 19, 1983, to Paul G. Schrader discloses polyglycidyl ethers of this (hydroxyphenyl) alkanes, their blends with other epoxy compounds, and their cured products.

U.S. Pat. No. 4,388,250, issued Jun. 14, 1983, to Farber et al., discloses a process for the preparation of p-Hydroxybenzyl-nitriles (note Table I, columns 7 and 8).

Other U.S. patents, which have related application and may be of interest, include U.S. Pat. No. 2,298,284; U.S. Pat. No. 3,366,684; U.S. Pat. No. 3,739,026; U.S. Pat. No. 3,225,098; U.S. Pat. No. 3,928,603; U.S. Pat. No. 5,047,592, and U.S. Pat. No. 4,394,496.

All of the above-cited prior art patents are incorporated herein by reference in their entirety.

SUMMARY OF THE INVENTION

The present invention relates to a method for the prevention of growth of algae by incorporating within liquids or coating on surfaces certain substituted amino alcohols. More precisely, this invention provides for algistat end uses for amino alcohol compounds endowed with chain extension which have the general formula:

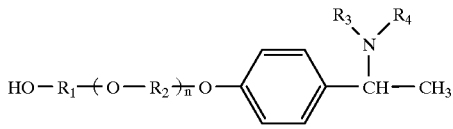

wherein n is 1-1000; and $R_1=R_2$, and $R_1$ and $R_2$ are from the croup consisting of —$CH_2$—$CH_2$—; —$CH_2$—$C(CH_3)H$—; and —$C(CH_3)H$—$CH_2$—; $R_3$, and $R_4$ are each independently selected from the group consisting of H, —$CH_3$, —$CH_2CH_3$, —$CH_2OH$, and —$CH_2$—$CH_2$—OH; and the diasteromeric salts thereof.

DETAILED DESCRIPTION OF THE PREFERRED EMBODIMENTS

The present invention provides a new use for certain amino alcohol compounds, which are derivatives of 4-hydroxyacetophenone, a well-known basic building block for numerous organic compounds. These novel amino alcohols have the general formula:

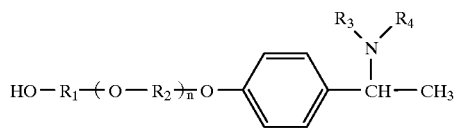

wherein:

n is 1 to 1000 (preferably 1-100);

$R_1=R_2$, and $R_1$ and $R_2$ are from the group:
—$CH_2$—$CH_2$—, —$CH_2$—$C(CH_3)$ H—, and —$C(CH_3)$ H—$CH_2$—

$R_3$ and $R_4$ are each independently selected from the group: —H, —$CH_3$, —$CH_2CH_3$, —$CH_2OH$, and —$CH_2$—$CH_2$—OH; and the diasteromeric salts thereof.

The compounds are useful as algistats. In particular, the compounds are useful as additives in paints, particularly water-based paints, coatings, polymers, paper manufacturing, swimming pools, decorative ponds and fountains, evaporative coolers (cooling towers), cleaning solutions, and the like water-containing materials. Solutions containing the compound may be used to treat surfaces as for example showers, bath compartments, saunas, steam rooms, and similar areas which are moisture. In certain areas of the world where the average humidity is high, a solution of the compounds may be used to treat roofs, walls, cloth used for clothing, tents, dining flies, ground cloths, and the like.

The compound useful for the present invention is prepared by reacting an alkali metal salt of 4-hydroxyacetophenone with an organic oxide, such as ethylene oxide or propylene oxide, in the presence of a suitable catalyst; then subjecting the reaction product to reductive amination under pressure to form the compound. Processes for the manufacture of the compound useful for the present invention are disclosed and claimed in U. S. Pat. No. 5,300.691.

Useful concentrations of the compound, when used to control the growth of algae in liquid applications, can be from about 1 to about 100 mg/L., preferably from about 2.5 to about 10 mg/L. For use, the compound is preferably dissolved in a minimum amount of a solvent therefore and then disbursed in the water at the desired concentration. Solvents may include alcohols, ketones, esters, ethers, and the like. When a compound is used to control the growth of algae on surfaces is can be applied to the surface as a solution in an appropriate solvent or from a slurry in any non-interferring liquid.

EXAMPLE

Test Compound: Compound (1) wherein n=30, $R_1=R_2$=—$CH_2$—$CH(CH_3)$—, and $R_3=R_4$=H Test Species: Freshwater green alga (*Selenastrum capricomutum*); 4-day old culture at test initiation Dilution Medium: Freshwater algal growth medium with an initial pH of 7.5+0.1; test temperature ranged from 23.0 to 25.6° C.

Nominal Concentrations: Control, 0.63, 1.25, 2.50, 5.00, and 10.0 mg whole material (wm)/L Study Length: 96 hours Results: The 96-hour EC50 to *S. capricornutum* was 1.38 mg wm/L (based on nominal concentrations). The 96-hour NOEC was 0.63 mg wm/L based on the lack of significant inhibitory effects observed at this test concentration.

The test substance was a golden brown viscous liquid and purity was >98%. The test substance was stored in the dark at ambient room temperature. Nominal test concentrations are reported as milligrams (mg) of compound as whole material (wm) per liter (L) of freshwater algal medium.

The freshwater alga tested was the green alga, *Selenastrum capricornutum* (UTEX #3648). The culture originated from an inoculum received from the University of Texas at Austin and maintained since Oct. 4, 1989. The algae were cultured on freshwater algal medium under continuous illumination yielding approximately 50 micromols per square meter per second (pmols/m$^2$/s). Cultures were maintained at approximately 24+2° C. prior to test initiation and were checked for purity weekly. The inoculum culture was 4 days old at test initiation.

The base water for the test medium was deionized water. The base water was sterilized and enhanced with reagent-grade nutrients. The pH of the test medium was adjusted to a pH of 7.5 with 0.1 N NaOH or HCl prior to use in the test. The test medium was filtered through a 0.45$\mu$ membrane filter prior to use.

Two static range-finding tests were conducted prior to performing the definitive test. Both tests were conducted at nominal test concentrations of 0.10, 1.00, 10.0, 100, and 1000 mg wm/L. The first test was aborted due to irregular algal growth among the controls and treatments. For the second range-finding test, inhibition of cell growth (based on cell number) compared to the pooled controls ranged from 23 percent at 1.00 mg wm/L to 99 percent at 1000 mg wm/L after 96 hours of exposure. There was a stimulation effect to algal growth (5%) at 0.10 mg wm/L. Undissolved chemical was observed at 100 and 1000 mg wm/L. Based upon these results, nominal test concentrations of 0.63, 1.25, 2.50, 5.00, and 10.0 mg wm/L were selected for the definitive test. The definitive exposure was conducted under static conditions in an environmentally controlled chamber set to provide a test temperature of 24+2° C.

A primary stock solution (100.040 mg wm/L) was prepared by weighing 1.0004 g of the test compound into a 10-ml volumetric flask and then bringing to volume with acetone. Four additional stocks (50,020; 25,010; 12,505; and 6,253 mg wm/L) were prepared by serial dilution starting with the primary stock. Each serially diluted stock solution was prepared by pipeting 5 ml of the appropriate stock solution into a 10 ml volumetric flask and bringing to volume with acetone. Test solutions (i.e., 10.0, 5.00, 2.50, 1.25, and 0.63 mg wm/L) were prepared by adding 40 $\mu$L of the appropriate stock solution to 400-mL volumes of filtered test medium. An algal test medium control and a solvent (acetone) control were maintained concurrently with the test solutions. The acetone concentration in the solvent control and all test solutions was 0.1 ml/L. Following stirring, pH measurements were taken and then four 100 ml aliquots of each test solution were transferred to sterilized 250-ml glass Erlenmeyer flasks (including one chemical blank). Three replicates were inoculated with algae while the fourth was established as a chemical "blank" control for each treatment and was not inoculated with algae. All flasks were capped with gas exchange caps.

The 96-hour exposure was initiated with the inoculation of approximately 10,000 cells/ml to each test flask (234 $\mu$l of an inoculum culture with a cell density of 428×10$^4$ cells/ml). The test chambers were randomly positioned in a temperature-controlled chamber under continuous fluorescent lighting and continuously swirled on an orbital shaker table at approximately 100 rpm (revolutions per minute). Test chambers were impartially re-positioned daily to eliminate position effects. Light intensity ranged between 35.3 and 63.3 (mols/m$^2$/s as measured by a LI-COR, Inc. Model LI-189 light meter equipped with a 2$\pi$ quantum sensor.

Algal growth was measured at least three times per inoculated flask by direct cell counts using an electronic particle counter (Coulter Counter Model Z1) every 24 hours. Morphological observations were also conducted on each test treatment daily using a compound microscope to detect abnormal cell morphology and coloration as compared to the control. Chemical "blanks" were counted concurrently with each test concentration to establish a background level, if any was present. To eliminate any effect of background during counting, the mean of the treatment blank was subtracted from the appropriate cell counts of the coinciding replicates prior to statistical analysis for all treatments and controls. All cell numbers presented in this report have already been corrected for any background detected.

After 96 hours, algal growth was maximally inhibited at nominal concentrations of 5.00 and 10.0 mg wm/L (i.e., either no algal growth or a net decrease in algal growth as compared to the initial inoculum); therefore, evaluation for algistatic versus algicidal response was necessary. This was accomplished by removing 0.5 ml aliquots of test solution containing growth-inhibited algae from each replicate test chamber.

These aliquots (1.5 mil total volume) were combined for each maximally inhibited test concentration into new test flasks and diluted with fresh (test substance free) algal medium to 100 ml, resulting in a test concentration of <0.15 mg wm/L (a nominal test substance concentration which did not affect growth as compared to the control). A control flask was also set up with an initial cell density of approximately 10,000 cells/ml to confirm acceptability of the procedures. The subcultures were incubated under the environmental conditions of the definitive test. The recovery phase was conducted for six days and was discontinued as soon as significant algal growth occurred in the maximally inhibited treatment. Algal growth was measured during the recovery phase by direct cell counts using a hemocytometer counting chamber with a compound microscope.

Temperature was measured in one uninoculated flask of test medium daily during the test. The temperature range of the environmentally controlled chamber was monitored using a minimum/maximum thermometer and the diurnal temperature ranges recorded daily. Light intensity was measured daily during the 96-hour exposure period at the level of the test solutions. The pH was measured at test initiation in the composites and at test termination in all control and test flasks using a Fisher Accumet® 1001 pH meter.

No water samples were collected or analyzed during the tests. Nominal concentrations were used during both the range-finding and definitive tests.

Algal growth response (as percent inhibition, I, or stimulation, S, in the test solutions compared to the controls) was calculated as follows:

% I=—(C—T)/C×100 or % S=(T—C)/C×100 where C=mean growth of the control and T=mean growth of treated culture. Mean and standard deviation of the algal responses were calculated and plotted for each treatment and control. Based on results of the test (percent inhibition of cell growth), the 96 hour $EC_{10}$, $EC_{50,}$ and $EC_{90}$ values with their 95 percent confidence limits were calculated.

After 96 hours of exposure, the percent inhibitor in cell numbers compared to the pooled controls ranged from 12 percent at 0.63 mg wm/L to 99+ percent at 5.00 and 10.0 mg wm/L. Daily mean cell counts and standard deviations for the control and test solutions are presented in Table 1. Growth curves show that algae in the controls and low treatments exhibited a pattern of-exponential growth during the 96-hour growth period. The coefficient of variation for cell numbers in the control was 4%.

Observations of cell morphology detected no differences in treated algal cells as compared to the control cells. The 96-hour $EC_{10}$, $EC_{50}$, and $EC_{90}$ values were calculated using the probit method to be 0~64, 1.38, and 2.97 mg wm/L, respectively. The NOEC was 0.63 mg wm/L, based on the lack of significant inhibitory effects observed at these test concentrations. No undissolved chemical was observed in the test medium during the test.

The measured test temperature during the 96-hour exposure ranged from 23.0 to 25.6° C.

The initial pH of the controls and all test solutions ranged from 7.1 to 7.5. All pHs were adjusted to 7.5+0.1 before inoculation with the algae at test initiation. After 96 hours, the pH ranged from 7.0 to 7.3 in the test solutions and from 7.2 to 7.8 in the controls.

In the recovery phase of the study, which was conducted to separate algistatic from algicidal effects of the test substance, significant growth of the algae was observed in all of the recovery treatments after 6 days of incubation. This demonstrated that the effect of the compound to the freshwater alga was algistatic in nature and not algicidal. The measured test-temperature during the 6-day recovery period ranged from 25.0 to 27.0° C. Light intensity ranged between 50.6 and 55.3 μmols/m2/s.

There were two deviations from the test protocol during the conduct of this study.

1. The stock algal culture was 4 days old at test initiation instead of 5–10 days as stated in the protocol. The initiation of the test was based on the growth conditions of the stock algae (pattern of exponential growth).
2. The test temperature during the recovery phase ranged from 25.0 to 27.0° C., slightly exceeding the range stated in the protocol (24+2° C.).

In the scientific opinion of the Study Director, these deviations did not affect the outcome or validity of the test results.

TABLE 1

Cell Numbers (as determined by an electronic particle counter) After 96 Hours of Continuous Exposure of the Green Alga, *Selenastrum capricornutum* Under Static Test Conditions

| Nominal Concentration | Mean Cell Numbers (x104, /ml) | | | | Percent |
|---|---|---|---|---|---|
| (mg wm/L) | 24 hr | 48 hr | 72 hr | 96 hr | Change |
| Control | 1.18 | 6.66 | 42.3 | 244 | — |
|  | (0.12) | (0.30) | (7~25) | (958) |  |
| Solvent Control | 1.26 | 6.60 | 35.8 | 226 | — |
|  | (0.35) | (2.14) | (9~33) | (23.2) |  |
| 0.63 | 1.37 | 6.40 | 38.3 | 208 | −12 |
|  | (0.25) | (1~19) | (3.74) | (1.33) |  |
| 1.25 | 1.15 | 4.54 | 23.9 | 142 | −40 |
|  | (0.31) | (2.97) | (18≠1) | (95.3) |  |
| 2.50 | 0.81 | 2.01 | 8.55 | 43.3 | −82 |
|  | (0.28) | (0.43) | (2.75) | (15.6) |  |
| 5.00 | 0.36 | 0.32 | 3.04 | 0.31 | −99+ |
|  | (0.28) | (0.27) | (4.43) | (0.52) |  |
| 10.0 | 0.02 | 0.02 | 0.00 | 1.12 | −99+ |
|  | (0~06) | (0.03) | (0.39) | (0.93) |  |
| Pooled Controls | 1.22 | 6.63 | 39.1 | 235 | — |

Values are means and standard deviations of triplicate test chambers; the standard deviations are presented in parentheses.
Percent inhibition as determined against pooled control cell numbers at 96 hours (235 × 104 cells/ml).
NOTE: Coefficient variation = Standard deviation × 100/Mean

What is claimed is:

1. A method for controlling the growth of algae in a liquid or upon a surface by use of a member of the group

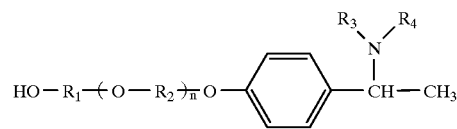

wherein n is 1-1000; and $R_1=R_2$, and $R_1$ and $R_2$ are from the croup consisting of —$CH_2$—$CH_2$—; —$CH_2$—$C(CH_3)H$—; and —$C(CH_3)H$—$CH_2$—; $R_3$, and R4 are each independently selected from the group consisting of H, —$CH_3$, —$CH_2CH_3$, —$CH_2OH$, and —$CH_2$—$CH_2$—OH; and the diasteromeric salts thereof.

2. A method of claim 1 wherein the growth of algae is controlled in a liquid by dissolving in the liquid from about 1 to about 100 mg/L of the compound.

3. A method of claim 1 wherein the growth of algae is controlled in a liquid by dissolving in the liquid from about 2.5 to about 10 mg/L of the compound.

4. A method of claim 1 wherein the growth of algae on surfaces is controlled by applying the compound to the surface.

5. A method of claim 4 wherein the compound is applied to the surface as a solution or as a slurry.

* * * * *